United States Patent
Decoster

(10) Patent No.: US 6,294,160 B1
(45) Date of Patent: *Sep. 25, 2001

(54) DETERGENT COSMETIC COMPOSITIONS FOR HAIR-CARE APPLICATION AND USE THEREOF

(75) Inventor: Sandrine Decoster, Epinay sur Seine (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,967

(22) PCT Filed: Jun. 6, 1997

(86) PCT No.: PCT/FR97/01009

§ 371 Date: Jan. 11, 1999

§ 102(e) Date: Jan. 11, 1999

(87) PCT Pub. No.: WO97/46212

PCT Pub. Date: Dec. 11, 1997

(30) Foreign Application Priority Data

Jun. 7, 1996 (FR) .................................................. 96 07194

(51) Int. Cl.⁷ ............................... A61K 7/06; A61K 7/50
(52) U.S. Cl. ................. 424/70.19; 424/70.1; 424/70.11; 424/70.12; 424/70.21; 424/70.22; 510/119; 510/123
(58) Field of Search ................................ 424/70.1, 70.11, 424/70.12, 70.19, 70.21, 70.22; 510/119, 123

(56) References Cited

U.S. PATENT DOCUMENTS

| 4,741,855 | 5/1988 | Grote et al. |
| 5,275,755 | 1/1994 | Sebag et al. |
| 5,308,551 | 5/1994 | Beauquey et al. |
| 5,536,493 | 7/1996 | Dubief |
| 5,571,458 | 11/1996 | Beauquey et al. |
| 6,221,817 | * 4/2001 | Guskey et al. |

FOREIGN PATENT DOCUMENTS

| 86967/91 | 5/1992 | (AU) . |
| 91177/91 | 7/1992 | (AU) . |
| 22349/92 | 1/1993 | (AU) . |
| 29272/92 | 6/1993 | (AU) . |
| 32092/93 | 8/1993 | (AU) . |
| 47068/93 | 3/1994 | (AU) . |
| 0 181 773 | 5/1986 | (EP) . |
| 0 285 389 | 10/1988 | (EP) . |
| 0 400 976 | 12/1990 | (EP) . |
| 0 413 417 A2 | 2/1991 | (EP) . |
| 0 473 508 | 3/1992 | (EP) . |
| 0 615 742 | 9/1994 | (EP) . |
| 92/10162 | 6/1992 | (WO) . |
| 93/18737 | 9/1993 | (WO) . |
| WO 94/16043 | 7/1994 | (WO) . |
| WO 97/14396 | 4/1997 | (WO) . |
| WO 97/35549 | 10/1997 | (WO) . |

OTHER PUBLICATIONS

Zviak, The Science of Hair Care, pp. 68, 70, 1986.*

* cited by examiner

Primary Examiner—Thurman K. Page
Assistant Examiner—Brian K. Seidleck
(74) Attorney, Agent, or Firm—Finnegan, Henderson, Farabow, Garrett & Dunner, L.L.P.

(57) ABSTRACT

A conditioning and detergent hair-care composition having one washing base with at least one anionic surfactant and at least one $C_{10}$–$C_{14}$ alkyl betaine amphoteric. surfactant, one conditioning system with at least one insoluble silicone, which is introduced into the composition in a non-emulsified form, and at least one $C_{16}$–$C_{18}$ acid ester of a polyol for suspending the insoluble silicone and for pearlizing the composition.

33 Claims, No Drawings

DETERGENT COSMETIC COMPOSITIONS FOR HAIR-CARE APPLICATION AND USE THEREOF

This application is a 371 of PCT/FR97/01009, filed Jun. 6, 1997.

The present invention relates to novel cosmetic compositions with improved properties, intended for simultaneously cleaning and conditioning the hair, and comprising, in a cosmetically acceptable support, a washing base consisting of surfactants with specific detergent power, in which specific insoluble silicones and fatty acid esters of polyols are also present as conditioners and as suspension agents and/or pearlescent agents, respectively. The invention also relates to the use of the said compositions in the abovementioned cosmetic application.

It is common practice to use detergent hair compositions (shampoos) based essentially on standard surfactants of anionic, nonionic and/or amphoteric type in particular, but more particularly of anionic type, to clean and/or wash the hair. These compositions are applied to wet hair and the lather generated by massaging or rubbing with the hands removes, after rinsing with water, the various types of soiling which are initially present on the hair.

Admittedly, these base compositions have good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fiber, this damage being associated in particular with the gradual removal of the lipids or proteins contained in or on the surface of this fiber.

Thus, in order to improve the cosmetic properties of the above detergent compositions, and more particularly those which are to be applied to sensitized hair (i.e. hair which has been damaged or made brittle, in particular under the chemical action of atmospheric agents and/or hair treatments such as permanent-waving, dyeing or bleaching), it is now common practice to introduce additional cosmetic agents known as conditioners into these compositions, these conditioners being intended mainly to repair or limit the harmful or undesirable effects induced by the various treatments or aggressions to which the hair fibers are subjected more or less repeatedly. These conditioners may, of course, also improve the cosmetic behavior of natural hair.

Among the conditioners most commonly used to date in shampoos, mention should be made of silicones and/or silicone derivatives, which give washed, dry or wet hair an ease of disentangling, softness and smoothness which are markedly better than that which can be obtained with the corresponding cleaning compositions from which they are absent. The suspending of the silicone and/or the pearlescent effect of the compositions can be obtained by means of acyl derivatives such as ethylene glycol stearate or diethylene glycol stearate (see in this respect EP 181,773 or EP 400, 976).

However, despite the progress made recently in the field of shampoos based on silicone polymers, these shampoos are not really completely satisfactory, and as such a strong need still exists currently as regards being able to provide novel products which give better performance with respect to one or more of the cosmetic properties mentioned above.

The present invention is directed towards satisfying such a need.

Thus, after considerable research conducted in this matter, the Applicant has now found, entirely surprisingly and unexpectedly, that by using a specific washing base, ie. a washing base combining at least one surfactant of anionic type and at least one amphoteric surfactant of $C_{10}$–$C_{14}$ alkylbetaine type comprising, as conditioners, specific and suitably selected silicones, as defined below, and $C_{16}$–$C_{18}$ acid esters of polyols, as agents for suspending the said silicones and/or pearlescent agent for the composition, it is possible to obtain detergent compositions with excellent cosmetic properties, in particular as regards the ease of styling, hold, liveliness, smoothness and suppleness of treated hair, as well as very good intrinsic washing power.

All of these discoveries form the basis of the present invention

Thus, according to the present invention, novel detergent and conditioning hair compositions are now proposed, comprising, in a cosmetically acceptable medium, (A) a washing base comprising at least one anionic surfactant and at least one amphoteric surfactant of $C_{10}$–$C_{14}$ alkylbetaine type, (B) a conditioning system comprising at least one insoluble silicone chosen from (i) polydialkylsiloxanes, (ii) polydiarylsiloxanes and (iii) polyalkylarylsiloxanes, the said silicone being introduced into the composition in non-emulsified form, and (C) a system for suspending the said silicone and/or for giving the composition a pearlescent effect, comprising at least one $C_{16}$–$C_{18}$ acid ester of polyols A subject of the invention is also the cosmetic use of the above compositions for cleaning and conditioning the hair.

However, other characteristics, aspects and advantages of the invention will emerge even more clearly on reading the description which follows, as well as the concrete, but in no way limiting, examples intended to illustrate it.

As indicated above, the essential components forming part of the composition of the haircare products according to the invention are (A) a washing base comprising (i) at least one anionic detergent surfactant and (ii) at least one amphoteric surfactant of $C_{10}$–$C_{14}$ alkylbetaine type, (B) a conditioning system comprising the insoluble silicone(s) and (C) the $C_{16}$–$C_{18}$ acid ester(s) of polyols for suspending the said silicone(s) and/or for giving the composition a pearlescent effect

A—WASHING BASE

The compositions in accordance with the invention necessarily comprise a washing base, which is generally aqueous.

The surfactant(s) forming the washing base comprise(s) one or more anionic surfactants and one or more $C_{10}$–$C_{14}$ alkylbetaine amphoteric surfactants.

The minimum amount of washing base is that which is just sufficient to give the final composition satisfactory foaming and/or detergent power, and excessive amounts of washing base do not really provide any additional advantages.

Thus, according to the invention, the washing base can represent from 4% to 50% by weight, preferably from 10% to 35% by weight and even more preferably from 12% to 25% by weight, relative to the total weight of the final composition.

According to a preferred characteristic of the hair compositions according to the present invention, the washing base contains no surfactants other than the anionic surfactants and the amphoteric surfactants of $C_{10}$–$C_{14}$ alkylbetaine type.

(i) Anionic Surfactant(s)

In the context of the present invention, their nature is not of truly critical importance.

Thus, as examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Use may also be made of weakly anionic surfactants, such as alkyl-D-galactosiduronic acids and their salts, and polyoxyalkylenated ether carboxylic acids and their salts, in particular those containing from 2 to 50 ethylene oxide groups, and mixtures thereof. Anionic surfactants such as polyoxyalkylenated carboxylic ether acids or salts are, in particular, those which correspond to formula (1) below:

$$R_1-(OCH_2H_4)_n-OCH_2COOA \qquad (1)$$

in which:

$R_1$ denotes an alkyl or alkylaryl group, and n is an integer or decimal (average value) which can range from 2 to 24 and preferably from 3 to 10, the alkyl radical having between 6 and 20 carbon atoms approximately, and aryl preferably denoting phenyl, A denotes H, ammonium, Na, K, Li, Mg or a monoethanolamine or triethanolamine residue. Mixtures of compounds of formula (1) can also be used, in particular mixtures in which the groups $R_1$ are different.

Among all of these anionic surfactants, it is more particularly preferred to use the alkyl sulphate and alkyl ether sulphate salts, and mixtures thereof.

(ii) Amphoteric Surfactant(s)

According to the invention, the amphoteric surfactants should be chosen from the ($C_{10}$–$C_{14}$) alkylbetaines of formula:

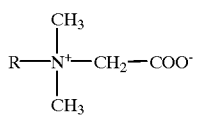

in which R denotes a linear or branched $C_{10}$–$C_{14}$ alkyl radical.

In particular, it is preferred to use the cocoylbetaine sold by the company Henkel under the name Dehyton AB 30.

B—CONDITIONING SYSTEM

According to an essential characteristic of the detergent hair compositions in accordance with the invention, these compositions also contain at least one specific insoluble silicone. This silicone should not have been introduced into the composition in the form of an emulsion.

According to the present invention, the term insoluble means insoluble in the final composition.

This silicone is chosen from (i) polydialkylsiloxanes, (ii) polydiarylsiloxanes and (iii) polyalkylarylsiloxanes.

The alkyl radicals contain especially from 1 to 10 carbon atoms and in particular denote methyl. The aryl radicals more particularly denote phenyl.

Among the polydialkylsiloxanes, mention may be made mainly of:

linear polydimethylsiloxanes containing trimethylsilyl end groups, such as, for example, and in a non-limiting manner, the Silbione oils of the series 70047 sold by Rhône-Poulenc, the oil 47 V 500 000 from Rhône-Poulenc or certain Viscasil oils from General Electric, and Fluid DC 200 from the company Dow Corning;

linear polydimethylsiloxanes containing hydroxydimethylsilyl end groups, such as the oils of the series 48 V from Rhône-Poulenc.

In this class of polydialkylsiloxanes, mention may also be made of the polydialkylsiloxanes sold by the company Goldschmidt under the trade names Abilwax 9800 and Abilwax 9801, which are polydi ($C_1$–$C_{20}$)-alkylsiloxanes.

Among the polyalkylarylsiloxanes, mention may be made of linear or branched polydimethylmethylphenyl-siloxanes or polydimethyldiphenylsiloxanes, such as the product DC 556 Cosmetic Grad Fluid from Dow Corning.

C—SYSTEM OF SUSPENDING AGENT(S) FOR SILICONE(S) AND/OR OF PEARLESCENT AGENT(S)

The compositions in accordance with the invention also necessarily comprise at least one $C_{16}$–$C_{18}$ acid ester of polyols as agent for suspending the silicone which forms part of the conditioning system and/or for giving the composition a pearlescent effect.

Mixtures of $C_{16}$ acid esters of a polyol and $C_{18}$ acid esters of a polyol are particularly preferred.

The $C_{16}$–$C_{18}$ acid esters of polyols can be chosen from the mono- and distearates of ethylene glycol, of polyethylene glycol, of glycerol, of propylene glycol and of polyglycerol and the mono- and dipalmitates of ethylene glycol, of polyethylene glycol, of glycerol, of propylene glycol and of polyglycerol, and mixtures thereof.

The polyethylene glycol and polyglyceryl esters contain from 2 to 150, and preferably from 2 to 20, ethylene glycol or glycerol groups.

It is preferred to use the mono- and distearates of ethylene glycol, the mono- and distearates of diethylene glycol, the mono- and distearates of triethylene glycol, the mono- and dipalmitates of ethylene glycol and the mono- and dipalmitates of glycerol.

It is possible, for example, to use the mixture (70/30 by weight) of ethylene glycol distearate and dipalmitate sold under the name Tegin BL 315 by the company Goldschmidt or ethylene glycol monopalmitate sold under the name Lanol P by the company SEPPIC.

As a guide, the detergent compositions in accordance with the invention generally have the following compositions:
(i) anionic surfactant(s): from 5 to 50% by weight, preferably from 5 to 20% by weight, relative to the total weight of the detergent composition;
(ii) amphoteric surfactant(s) of alkylbetaine type: from 1 to 50% by weight, preferably from 1 to 20% by weight, relative to the total weight of the composition In addition, the concentration of amphoteric surfactants is generally from 5 to 70% by weight, and preferably from 10 to 30% by weight, relative to the total weight of the anionic surfactant(s) present in the detergent formulation;

(iii) $C_{16}$–$C_{18}$ acid ester(s) of polyol(s): from 0.05% to 10% by weight, preferably from 0.1% to 5% by weight and even more preferably from 0.1% to 4% by weight, relative to the total weight of the final composition;

(iv) insoluble silicone(s) not pre-emulsified: from 0.05% to 10%, preferably between 0.1% and 5% and even more preferably between 0.2% and 3%, relative to the total weight of the composition.

The vehicle, or support, for the detergent compositions according to the invention is preferably water or an aqueous-alcoholic solution of a lower alcohol such as ethanol, isopropanol or butanol.

The detergent compositions according to the invention have a final pH generally of between 3 and 9. Preferably, this pH is between 5 and 7. The pH can be adjusted to the desired value conventionally by adding a base (organic or inorganic) to the composition, for example aqueous ammonia or a primary, secondary or tertiary (poly)amine such as monoethanolamine, diethanolamine, triethanolamine, isopropanolamine or 1,3-propanediamine, or alternatively by adding an acid, preferably a carboxylic acid such as, for example, citric acid.

Needless to say, the detergent compositions according to the invention can also contain any common adjuvant encountered in the shampoo sector, such as, for example, fragrances, preserving agents, sequestering agents, thickeners, softeners, foam modifiers, dyes, pearlescent agents, moisturizers, antidandruff agents, anti-seborrhoeic agents, vitamins, sunscreens and the like.

Needless to say, a person skilled in the art will take care to select this or these optional complementary compounds and/or the amounts thereof such that the advantageous properties intrinsically associated with the quaternary combination (anionic surfactant+amphoteric surfactant of alkylbetaine type+$C_{16}$–$C_{18}$ acid ester of a polyol+specific insoluble silicone) in accordance with the invention are not, or are not substantially, adversely affected by the addition or additions envisaged.

These compositions can be in the form of more or less thickened liquids, creams or gels and they are mainly suitable for washing, caring for and/or styling the hair.

When the compositions in accordance with the invention are used as standard shampoos, they are simply applied to wet hair and the lather generated by massaging or rubbing with the hands is then removed, after optionally leaving it to stand on the hair for a period of time, by rinsing with water, it being possible for the operation to be repeated one or more. times.

As indicated above, the compositions in accordance with the invention give the hair, after rinsing, a remarkable treating effect which is reflected in particular in an ease of disentangling and of styling, as well as smoothness and softness, which are markedly improved.

A subject of the invention is also a process for washing and conditioning keratin fibers such as the hair, which consists in applying an effective amount of a composition as defined above to the said wet fibers and then in rinsing them with water, after optionally leaving it to stand on the fibers for a period of time.

A concrete, but in no way limiting, example illustrating the invention will now be given.

EXAMPLE

A shampoo composition was prepared, containing:

| | | |
|---|---|---|
| Sodium lauryl ether sulphate (70/30 C12/C14) containing 2.2 mol of ethylene oxide (AM = active material) | | 14 g AM |
| Cocoylbetaine as an aqueous solution containing 32% active material (Dehyton AB 30 from Henkel) | | 2.56 g AM |
| Insoluble silicone (*) | | 2.7 g |
| Ethylene glycol distearate and dipalmitate (Tegin BL 315 from Goldschmidt) | | 2.5 g |
| Coconut acid monoisopropanolamide | | 0.65 g |
| Citric acid | qs | pH 7 |
| Demineralized water | qs | 100 g |

(*): Polydimethylsiloxane sold under the name Mirasil DM 500 000 by the company Rhône-Poulenc, used and introduced as supplied into the composition to be prepared.

Shampooing is carried out by applying about 12 g of the composition to premoistened hair. The shampoo is worked into a lather and is then rinsed out thoroughly with water.

A panel of experts found that the compositions in accordance with the invention give the hair, after rinsing, a remarkable treating effect which is reflected in particular in a remarkable ease of disentangling and of styling, as well as remarkable smoothness and softness of the hair.

What is claimed is:

1. A detergent and conditioning hair composition comprising (A) a washing base comprising at least one anionic surfactant and at least one $C_{10}$–$C_{14}$ alkylbetaine amphoteric surfactant, (B) a conditioning system comprising at least one insoluble silicone, wherein said at least one insoluble silicon is chosen from (i) polydialkylsiloxanes, (ii) polydiarylsiloxanes, and (iii) polyalkylarylsiloxanes, further wherein said at least one insoluble silicone is introduced into the composition in non-emulsified form, and (C) a system for suspending said silicone, for giving the composition a pearlescent effect, or both, wherein said system comprises at least one $C_{16}$–$C_{18}$ acid ester of a polyol, and further wherein said washing base is free of surfactants other than anionic surfactants and $C_{10}$–$C_{14}$ alkylbetaine amphoteric surfactants.

2. A composition according to claim 1, wherein said composition further comprises a cosmetically acceptable medium, and further wherein said at least one anionic surfactant is present in a proportion ranging from 5 to 50% by weight, relative to the total weight of the composition.

3. A composition according to claim 2, wherein said at least one anionic surfactant is present in a proportion ranging from 5 to 20% by weight, relative to the total weight of the composition.

4. A composition according to claim 1, wherein said at least one amphoteric surfactant is present in a proportion ranging from 1 to 50% by weight, relative to the total weight of the composition.

5. A composition according to claim 4, wherein said at least one amphoteric surfactant is present in a proportion ranging from 1 to 20% by weight, relative to the total weight of the composition.

6. A composition according to claim 1, wherein said at least one amphoteric surfactant is present in a proportion ranging from 5 to 70% by weight, relative to the total weight of said at least one anionic surfactant.

7. A composition according to claim 6, wherein said at least one amphoteric surfactant is present in a proportion ranging from 10 to 30% by weight, relative to the total weight of said at least one anionic surfactant.

8. A composition according to claim 1, wherein said at least one amphoteric surfactant is cocoylbetaine.

9. A composition according to claim 1, wherein said at least one $C_{16}$–$C_{18}$ acid ester of a polyol is chosen from mono- and distearates of ethylene glycol, of polyethylene glycol, of glycerol, of propylene glycol and of polyglycerol or is chosen from mono- and dipalmitates of ethylene glycol, of polyethylene glycol, of glycerol, of propylene glycol and of polyglycerol.

10. A composition according to claim 9, wherein said at least one $C_{16}$–$C_{18}$ acid ester of a polyol is chosen from mono- and distearates of ethylene glycol, mono- and distearates of diethylene glycol, mono- and distearates of triethylene glycol, mono- and dipalmitates of ethylene glycol, mono- and dipalmitates of diethylene glycol and mono- and dipalmitates of triethylene glycol.

11. A composition according to claim 1, wherein said polydialkylsiloxanes are chosen from polydimethylsiloxanes containing trimethylsilyl end groups, and polydimethylsiloxanes containing hydroxydimethylsilyl end groups.

12. A composition according to claim 1, wherein said at least one $C_{16}$–$C_{18}$ acid ester of a polyol is present in a proportion ranging from 0.05% to 10% by weight, relative to the total weight of the composition.

13. A composition according to claim 12, wherein said at least one $C_{16}$–$C_{18}$ acid ester of a polyol is present in a proportion ranging from 0.1% to 5% by weight, relative to the total weight of the composition.

14. A composition according to claim 13, wherein said at least one $C_{16}$–$C_{18}$ acid ester of a polyol is present in a proportion ranging from 1% to 4% by weight, relative to the total weight of the composition.

15. A composition according to claim 1, wherein said at least one insoluble silicone is present in a proportion ranging from 0.05% to 10% by weight, relative to the total weight of the composition.

16. A composition according to claim 15, wherein said at least one insoluble silicone is present in a proportion ranging from 0.1% to 5% by weight, relative to the total weight of the composition.

17. A composition according to claim 16, wherein said at least one insoluble silicone is present in a proportion ranging from 0.2% to 3% by weight, relative to the total weight of the composition.

18. A composition according to claim 1, said composition having a pH ranging from 3 to 9.

19. A composition according to claim 18, said composition having a pH ranging from 5 to 7.

20. A composition according to claim 1, wherein said composition is an aqueous or aqueous-alcoholic composition.

21. A method for cleaning and/or conditioning hair, said method comprising applying to said hair an effective amount of the detergent and conditioning composition according to claim 1.

22. The method according to claim 21, wherein said method further comprises wetting said hair before the application of said detergent and conditioning composition.

23. The method according to claim 22, wherein said method further comprises rinsing said hair following the application of said detergent and conditioning composition.

24. The method according to claim 23, wherein said method further comprises allowing said composition to remain on said wetted hair after said application and before said rinsing.

25. The composition according to claim 1, which composition is in the form of a thickened liquid, a cream, a gel, or a rinse-out lotion.

26. A composition according to claim 1, wherein said at least one $C_{10}$–$C_{14}$ alkylbetaine amphoteric surfactant is an alkylbetaine of the formula:

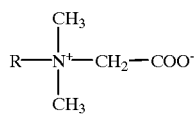

wherein R denotes a linear or branched $C_{10}$–$C_{14}$ alkyl radical.

27. A composition according to claim 1, wherein said washing base is present in a proportion ranging from 4 to 50% by weight, relative to the total weight of the composition.

28. A composition according to claim 27, wherein said washing base is present in a proportion ranging from 10 to 35% by weight, relative to the total weight of the composition.

29. A composition according to claim 28, wherein said washing base is present in a proportion ranging from 12 to 25% by weight, relative to the total weight of the composition.

30. A composition according to claim 1, wherein said polydialkylsiloxanes are chosen from polydialkylsiloxanes containing $C_1$–$C_{10}$ alkyl groups.

31. A composition according to claim 30, wherein said polydialkylsiloxanes are chosen from polydimethylsiloxanes.

32. A composition according to claim 1, wherein said polydiarylsiloxanes are chosen from polydiphenylsiloxanes.

33. A composition according to claim 1, wherein said at least one $C_{16}$–$C_{18}$ acid ester of a polyol is a mixture of a $C_{16}$ acid ester of a polyol and a $C_{18}$ acid ester of a polyol.

* * * * *

UNITED STATES PATENT AND TRADEMARK OFFICE
CERTIFICATE OF CORRECTION

PATENT NO.    : 6,294,160 B1
DATED         : September 25, 2001
INVENTOR(S)   : Sandrine Decoster It is certified that error appears in the above-identified patent and that said Letters Patent is hereby corrected as shown below:

<u>Title page,</u>
Item [57], ABSTRACT,
Line 3, after "amphoteric", delete the period.

<u>Column 6, claim 1,</u>
Line 34, "insoluble silicon" should read -- insoluble silicone --.

<u>Column 7, claim 13,</u>
Line 28, "$C_{16}$-$C_{18}$acid" should read -- $C_{16}$-$C_{18}$ acid --.

Signed and Sealed this

Twenty-sixth Day of March, 2002

*Attest:*

JAMES E. ROGAN
*Attesting Officer*   *Director of the United States Patent and Trademark Office*